United States Patent
Erkamp et al.

(10) Patent No.: US 10,116,069 B2
(45) Date of Patent: Oct. 30, 2018

(54) CONNECTOR FOR NEEDLE WITH PIEZOELECTRIC POLYMER SENSORS

(71) Applicant: KONINKLIJKE PHILIPS N.V., Eindhoven (NL)

(72) Inventors: Ramon Quido Erkamp, Swampscott, MA (US); Ameet Kumar Jain, Boston, MA (US); Francois Guy Gerard Marie Vignon, Croton On Hudson, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 31 days.

(21) Appl. No.: 15/302,703

(22) PCT Filed: Apr. 7, 2015

(86) PCT No.: PCT/IB2015/052490
§ 371 (c)(1),
(2) Date: Oct. 7, 2016

(87) PCT Pub. No.: WO2015/155671
PCT Pub. Date: Oct. 15, 2015

(65) Prior Publication Data
US 2017/0033474 A1  Feb. 2, 2017

Related U.S. Application Data

(60) Provisional application No. 61/978,220, filed on Apr. 11, 2014.

(51) Int. Cl.
*H01R 9/05* (2006.01)
*H01R 24/58* (2011.01)
(Continued)

(52) U.S. Cl.
CPC .......... *H01R 9/05* (2013.01); *A61B 17/3403* (2013.01); *H01R 13/502* (2013.01);
(Continued)

(58) Field of Classification Search
CPC ...... H01R 9/05; H01R 13/502; H01R 13/508; H01R 24/58; H01R 13/6593;
(Continued)

(56) References Cited

U.S. PATENT DOCUMENTS

| 6,217,518 B1 | 4/2001 | Holdaway |
| 2009/0317965 A1 | 12/2009 | Jacobs |
| 2013/0217258 A1 | 8/2013 | Blasick |

FOREIGN PATENT DOCUMENTS

WO   2013154922 A1   10/2013

OTHER PUBLICATIONS

Barr, Richard G. "Improved Needle Visualization with Electronic Beam Steering", Ultrasound Quarterly, vol. 28, No. 2, Jun. 2012.
(Continued)

*Primary Examiner* — Khiem Nguyen (57) ABSTRACT

A connector includes an inner conductive body for connecting to a sensor contact on a medical device. An insulator is formed on the inner conductive body. An outer conductive body is formed over the insulator and surrounds the inner conductive body but is electrically isolated from the inner conductive body. The outer conductive body is for making contact at two places on a medical needle on opposite sides of the inner conductive body.

15 Claims, 7 Drawing Sheets

(51) Int. Cl.
*H01R 13/502* (2006.01)
*H01R 13/508* (2006.01)
*A61B 8/08* (2006.01)
*H01R 103/00* (2006.01)
*H01R 13/6593* (2011.01)
*A61B 17/34* (2006.01)
*A61B 90/00* (2016.01)

(52) U.S. Cl.
CPC ........... *H01R 13/508* (2013.01); *H01R 24/58* (2013.01); *A61B 8/0841* (2013.01); *A61B 2017/3413* (2013.01); *A61B 2090/3925* (2016.02); *H01R 13/6593* (2013.01); *H01R 2103/00* (2013.01); *H01R 2201/12* (2013.01)

(58) Field of Classification Search
CPC ............ H01R 2103/00; H01R 2201/12; A61B 17/3403; A61B 2090/3925; A61B 8/0841; A61B 2017/3413
USPC ............................................ 439/578, 607.34
See application file for complete search history.

(56) References Cited

OTHER PUBLICATIONS

Nichols, Kremer et al "Changes in Ultrasonographic Echogenicity and Visibility of Needles with Changes in Angles of Insonation", J Vasc Interv Radiology, vol. 14, No. 12, 2003.
Cheung, Stphanic et al "Enhancement of needle visibility in ultrasound-guided percutaneous procedures", Ultrasound in Medicine & Biology, vol. 30, Issue 5, May 2004—Abstract Only.

CONNECTOR FOR NEEDLE WITH PIEZOELECTRIC POLYMER SENSORS

CROSS-REFERENCE TO PRIOR APPLICATIONS

This application is the U.S. National Phase application under 35 U.S.C. § 371 of International Application No. PCT/IB2015/052490, filed on Apr. 7, 2015, which claims the benefit of U.S. Provisional Patent Application No. 61/978,220, filed on Apr. 11, 2014. These applications are hereby incorporated by reference herein.

RELATED APPLICATION INFORMATION

This application claims priority to U.S. provisional application Ser. No. 61/978,220, filed on Apr. 11, 2014, incorporated herein by reference in its entirety.

BACKGROUND

Technical Field

This disclosure relates to medical instruments and more particularly to a connector device or system to connect a device having ultrasound receivers formed thereon to an imaging system.

Description of the Related Art

In ultrasound imaging, the visibility of a needle is often very poor due to the specular nature of the needle surface that reflects beams away from the imaging probe. To alleviate this problem some needle manufacturers have produced needles with special echogenic coatings, but the visualization improvement is limited. Ultrasound imaging system manufacturers have developed algorithms that use multiple imaging beams from varied angles, but improvement is limited and such a strategy is primarily suited only for linear arrays. Both strategies do not help when the needle is inserted perpendicular to the imaging plane or the needle path has a small offset relative to the imaging plane.

One solution that has been proposed to visualize the tip of interventional tools such as needles, but also catheters, is to add ultrasound receivers near the tip of the tool. While the imaging beam sweeps the field of view, the signals from the sensors indicate how close the beams are getting to the sensor. This information is used to calculate sensor position relative to the ultrasound image with positional accuracy exceeding 0.5 mm, even under conditions where the needle is not visible in the ultrasound image. The sensor needs to not interfere with the functionality of the device (e.g., an automatic biopsy device), that is, not block the lumen, not interfere with the mechanics, etc.

SUMMARY

In accordance with the present principles, a connector includes an inner conductive body for connecting to a sensor contact on a medical device. An insulator is formed on the inner conductive body. An outer conductive body is formed over the insulator and surrounds the inner conductive body but is electrically isolated from the inner conductive body. The outer conductive body is for making contact at two places on a medical device on opposite sides of the inner conductive body.

Another connector includes a first conductive body configured to receive therein a medical instrument with a circular cross-section. The first conductive body contacts an outer surface of the medical instrument at a first electrical contact and at a second electrical contact. The first conductive body forms a cavity. A second conductive body is disposed within the cavity and contacts the outer surface of the medical instrument at a third electrical contact. The third electrical contact is disposed between the first and the second electrical contact. An insulating material is disposed between the first and second conductive body in the cavity to electrically isolate the first and second conductive bodies from each other. A coaxial cable has a center conductor and a shield, wherein the central conductor and the shield each connect to one of the first and second conductive bodies.

Yet another connector includes a needle having an ultrasonic sensor formed on the needle. The sensor is connected to a sensor contact on a hub end portion of the needle by an electrical trace. The electrical trace has a shield formed over the trace. An inner conductive body connects to the sensor contact. An insulator is formed on the inner conductive body and an outer conductive body is formed over the insulator and surrounds the inner conductive body but is electrically isolated from the inner conductive body. The outer conductive body makes contact to the needle and the shield on opposite sides of the inner conductive body. An insulating coating is formed on an outer surface of the outer conductive body. A coaxial cable has a center conductor and a coaxial shield wherein the central conductor connects to the inner conductive body and the coaxial shield connects to the outer conductive body.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

In accordance with the present principles, a device, system and method for connecting a needle or other device to an imaging system are provided that minimize cost on the disposable needle side and permit for a non-disposable needle connecting device. In one particularly useful embodiment, at a hub end portion (proximal end portion), a bare needle surface, a signal trace ring electrode and an outer shield form three circular contact pads. A small connector is disclosed that is configured to clamp onto the three circular contact pads.

The design of the connector minimizes cost on the disposable needle and puts the more costly part of the connection on a reusable clamp that attaches to the needle. The present embodiments can be implemented using additive manufacturing technologies such as, for example, conformal micro dispensing systems or inkjet deposition techniques. The needle or other device may include one or more ring contact pad structures at a needle hub end portion. The one or more ring contact pad structures provide connection points for ultrasonic receivers or other components formed on or integrated with the needle or other device. The needle or other device preferably provides for low disposable cost. A specialized non-disposable/reusable connector clamps or is molded onto a contact pad structure. In one embodiment, the reusable connector has an opened and closed position. In the open position, the needle can be positioned within the connector. In the closed position, a set of contact electrodes press against the needle contact pads, and the needle is held firmly in place by a clamping mechanism of the connector.

It should be understood that the present invention will be described in terms of medical instruments; however, the teachings of the present invention are much broader and are applicable to any connector that connects to an instrument with multiple connection points. In some embodiments, the present principles are employed in making low profile connections to medical instruments or other biological or mechanical systems. In particular, the present principles are applicable to equipment for use in internal tracking procedures of biological systems and are applicable for procedures in all areas of the body such as the lungs, gastrointestinal tract, excretory organs, blood vessels, etc. The elements depicted in the FIGS. may be implemented in various combinations of hardware and software and provide functions which may be combined in a single element or multiple elements.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

It will also be understood that when an element such as a layer, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Figure 1:
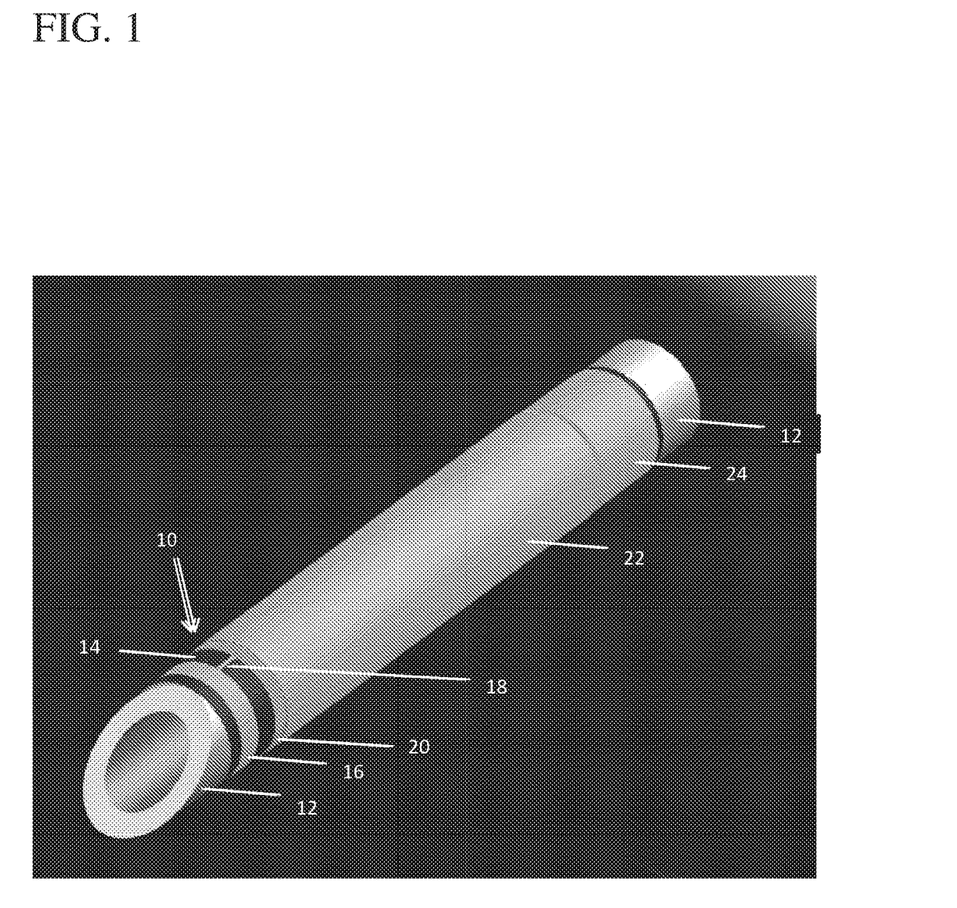
FIG. 1 is a perspective view showing a needle with a sensor formed thereon and with three circular contacts on a hub end portion in accordance with the present principles.

Referring now to the drawings in which like numerals represent the same or similar elements and initially to FIG. 1, a needle 12 with an integrated ring sensor 10 has ring shaped contacts regions, which include a shield 22, a hub contact 24 and a proximal end portion of a needle 12. The needle 12 preferably includes a metal, such as a stainless steel although other surgically compatible materials may be employed. An insulator 14 is deposited or printed on the needle 12. The insulator 14 may include any suitable dielectric material that adheres to the needle 12. The insulator 14 is deposited on the needle 12 without covering a small section at the tip region. This small section of the needle 14 is coated with a piezoelectric copolymer (not shown). The metal needle 12 serves as a bottom electrode in this illustrative embodiment. In one embodiment, the copolymer includes a P(VDF-TrFE) ring, although other suitable materials may be employed. A top electrode 16 and a signal trace 18 connecting to the top electrode 16 are applied. The top electrode 16 is formed over the copolymer, and the trace is formed over a portion of the insulator 14. The top electrode 16 and the trace 18 may be printed using a conductive ink. Other processes may be employed as well, such as, e.g., masked vapor deposition or vapor deposition and etching.

The top electrode 16 and the trace 18 may have a thickness of less than one micron to a few microns.

Another insulator 20 is formed over the trace 18 and insulator layer 14. This insulator 20 may be produced by dip coating from the proximal end of the needle 12. The insulator 20 is deposited or printed on the needle 12. The insulator 20 may include any suitable dielectric material that adheres to underlying materials. The insulators 14, 20 may each be about 25-50 microns thick although other thicknesses may be employed.

The conductive shield 22 is applied over the insulator 20. The conductive shield 20 may be produced by vapor deposition or dip coating in conductive ink. Care needs to be taken to not cover the tip (distal end portion of the needle 12). The needle 12 and outer shield 22 will be coupled together as they form a driven shield. To electrically insulate the top electrode 16 from the surroundings and ensure biocompatibility, the whole needle could be covered with, for example, parylene or other outer dielectric material (not shown). If the parylene coating (outer dielectric) is extremely thin, there may be a capacitive coupling from the top electrode 16 to a body (where the needle 12 will be inserted) and the body to the outer shield 22. With a conductive body, this could create a shunt path across the sensor 10 and thus form a low pass filter. Care needs to be taken that the cut off frequency is significantly above the ultrasound frequency of interest. Alternatively, the outer dielectric and outer shield 22 could be made to go over the tip, thereby insulating the top electrode 16 (but possibly slightly degrade sensitivity as the acoustic wave has to pass through it). By properly selecting acoustic properties and thickness the outer dielectric may serve as an acoustic matching layer.

For the dielectric layers, e.g., insulator 14, 20 and the outer dielectric, it is advantageous to select a material with a relatively low dielectric constant, for example, polytetrafluoroethylene (PTFE), polypropylene, other plastics/polymers, such as polyurethane. Other materials may also be employed.

The hub contact 24 may be formed with the shield 22. The hub contact 24 connects to the top electrode 16 via the trace 18. The narrow trace 18 minimizes the capacitive loading of the sensor 10. The thin interconnect trace 18 is shielded similarly to a stripline configuration to be optimized for low capacitance. The sensor 10 can be more sensitive to injected noise as the needle 12, that is in electrical contact with tissue (when filled with fluid or stylet), is part of the interconnect.

The contact pad 24 of the top electrode 16 is formed at a hub end (proximal end portion) and provides for low disposable cost connectivity. Specialized electronics can be provided to reduce signal loss due to capacitive loading of the interconnect.

The present principles can be extended to multiple sensors on a same needle. This permits a determination of orientation of the needle and also determination of the location of the needle tip without the need to place the sensor very close to the tip. Calculating the tip location based on signals from multiple sensors should also increase the measurement accuracy as well as provide an indication of confidence in the measurement. The cost is a slightly more complicated manufacturing process and a slight loss of signal because of the extra capacitive load of multiple sensors.

For the present example, the needle 12 has ring shaped contact pads 22, 24, 12 at the hub end portion (proximal end portion) deposited directly onto the needle 12. The needle 12 acts as a signal lead for the sensor 10. At the hub end, the bare needle 12 forms one contact. Dielectric layer 14 insulates the signal trace 18 from the needle surface. The contact pad 24 forms an electrode connected to the thin signal trace 18 (which also connects to the top electrode 16). The outer insulation layer 20 separates the signal trace 18 from the outer shield 22.

Figure 2:
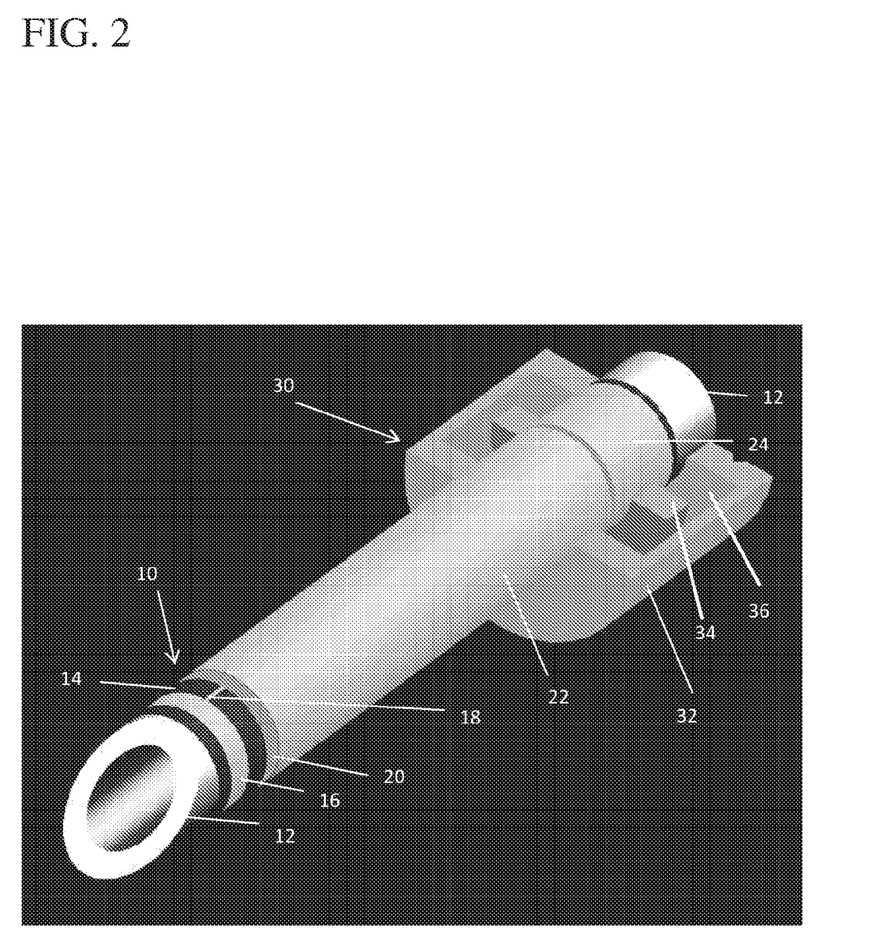
FIG. 2 is a perspective view showing the needle of FIG. 1 having an inner conductive body and an outer conductive body formed or placed thereon in accordance with the present principles.

Referring to FIG. 2, a connector 30 is shown in accordance with one illustrative embodiment. The connector 30 includes two conductive portions 32 and 34. The conductive portions 32 and 34 may be formed from a conductive polymer, such as, a conductive silicone, e.g., ssp550-45 commercially available from Specialty Silicone Products, Inc. (sspinc.com). The connector 30 is shown split-half to make the interior of the connectors 30 visible. The conductive polymer structures of portions 32 and 34 connect to the ring electrodes 12, 24 and 22. The needle hub 12 and outer shield 22 in this embodiment need to be electrically connected to each other. This is to create a stripline-like connection from hub to sensor. The portion 32 makes the connection between outer shield 22 and needle 12, and at the same time completely shields the inner conductive polymer of portion 34. Portion 34 connects to the signal trace electrode or contact pad 24. The portion 34 is separated in all dimensions from the portion 32 by a void, cavity or space 36.

Figure 3:
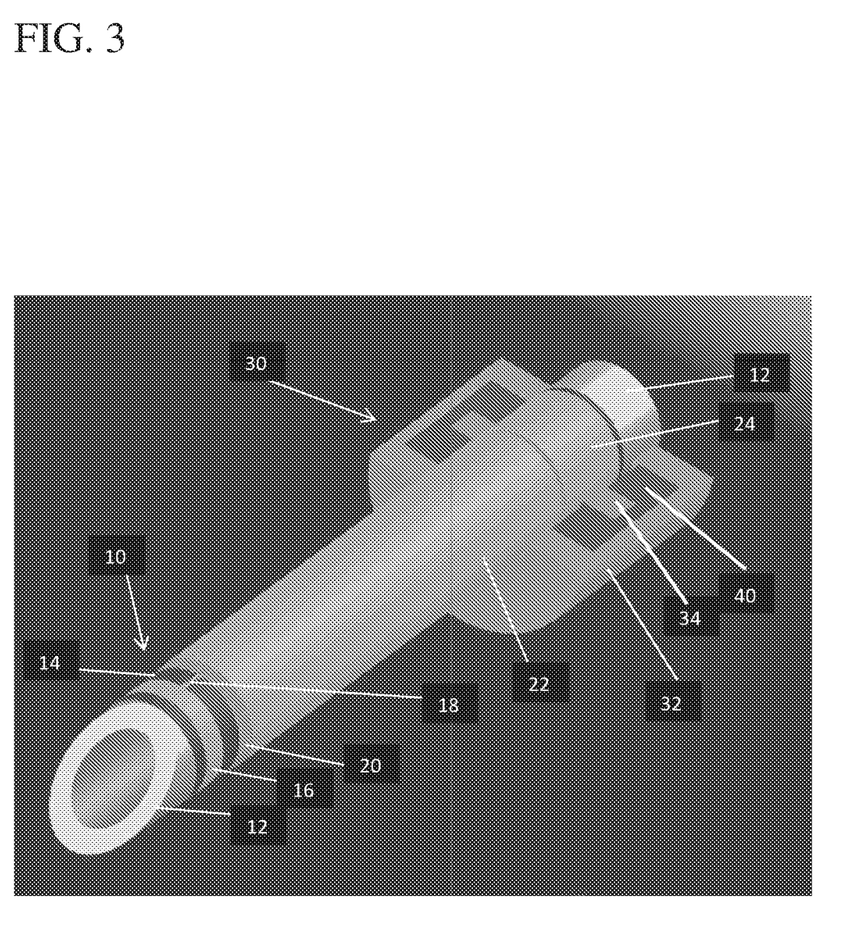
FIG. 3 is a perspective view showing the needle of FIG. 2 having an insulating material disposed between the inner conductive body and the outer conductive body in accordance with the present principles.

Referring to FIG. 3, the space 36 is filled with an electrically insulating material 40. The conductive polymers 32, 34 are held together by the electrically insulating material 40. The insulating material 40 may include, for example, polypropylene, polyurethane, acrylonitrile butadiene styrene (ABS), polycarbonate or other dielectric materials.

Figure 4:
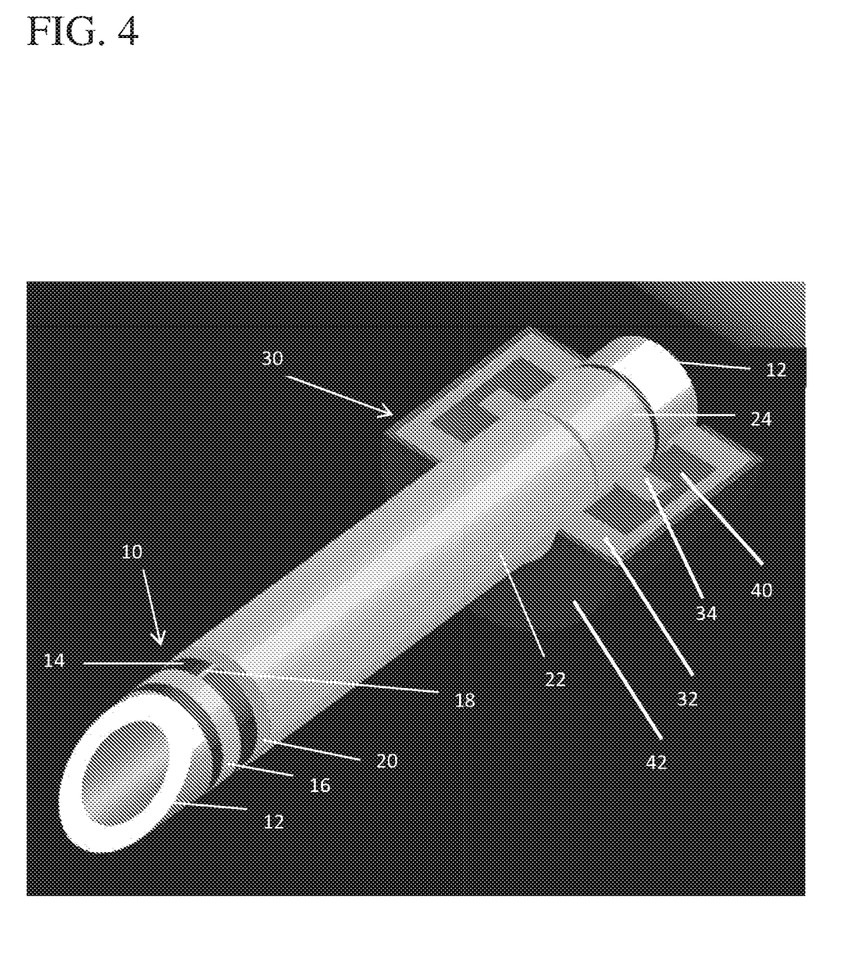
FIG. 4 is a perspective view showing the needle of FIG. 3 having an insulating material formed on the outer conductive body in accordance with the present principles.

Referring to FIG. 4, the connector 30 may include an outer insulating layer 42. The outer insulating layer 42 is added to the connector 30. The outer insulating layer 42 may employ any suitable dielectric material, e.g., parylene, polyurethane, etc.

Figure 5:
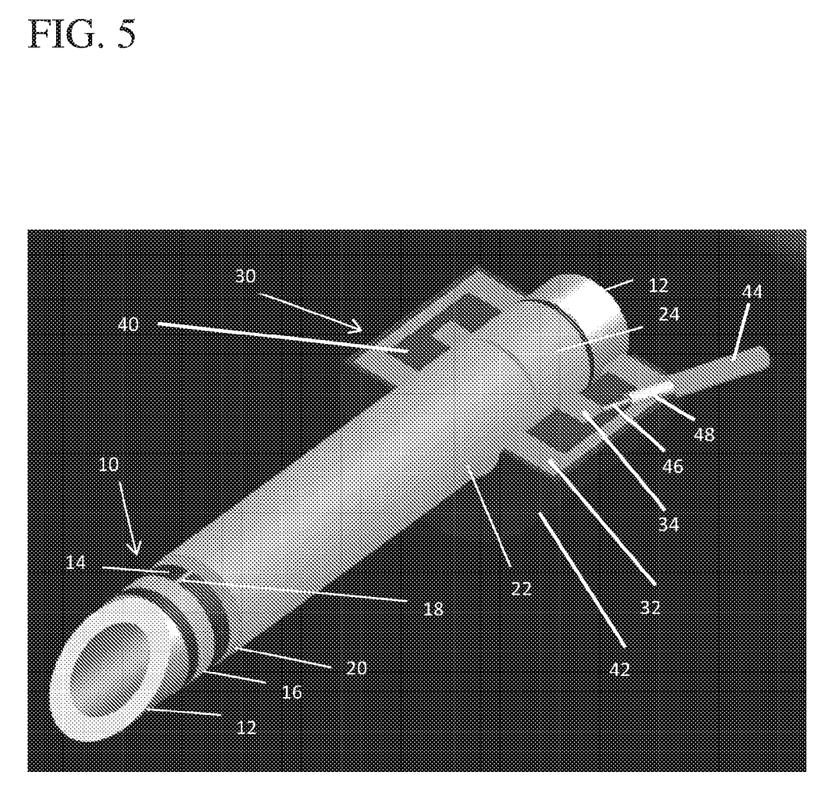
FIG. 5 is a perspective view showing the needle of FIG. 4 having a coaxial cable with portions connected to the inner conductive body and the outer conductive body in accordance with the present principles.

Referring to FIG. 5, a coaxial cable 44 is attached to the connector 30. A central conductor 46 of the cable 44 is connected to the inner conductive polymer of portion 34, and a coaxial shield 48 is connected to the outer conductive polymer of portion 32. The coaxial cable 44 may be attached by soldering, conductive adhesive, or simply mechanically held between split sections of the connector 30 (e.g., in a clamshell arrangement).

Figure 6:
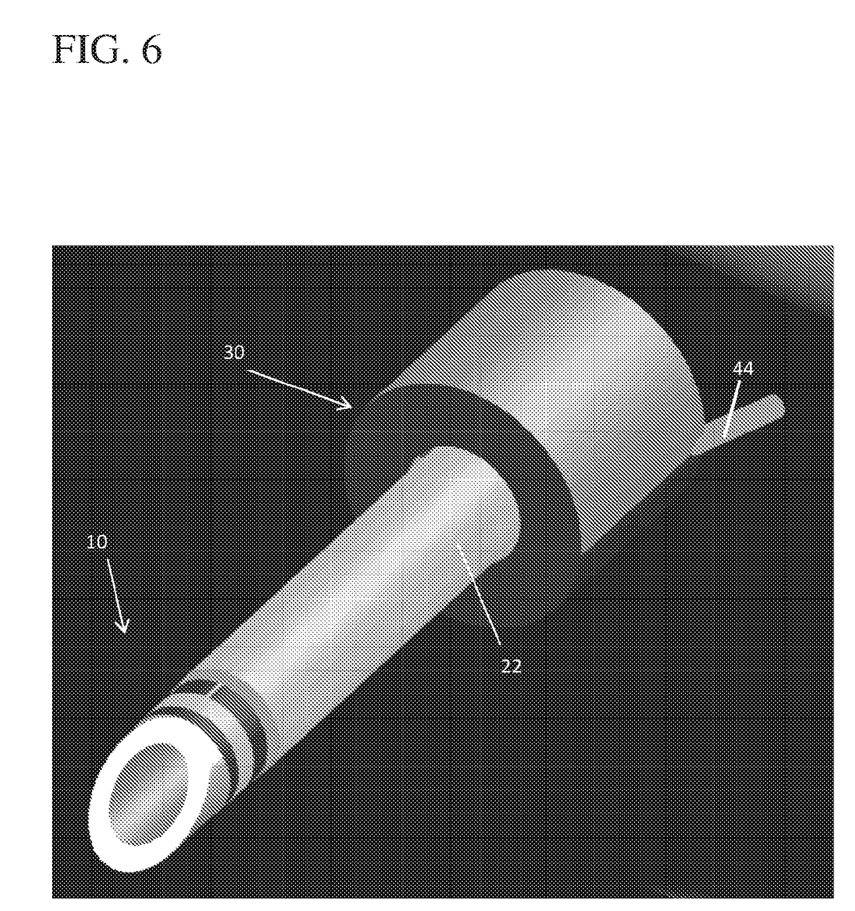
FIG. 6 is a perspective view showing a connector formed over or placed on the needle of FIG. 1 having a coaxial cable for connecting to electronics in accordance with the present principles.

Referring to FIG. 6, a completed connector 30 is illustratively shown. In one embodiment, the connector 30 may be completed by applying another split-half structure over the first split-half structure (clam-shell configuration). The clam shell configuration can be implemented by placing the needle 12 with sensor 10 thereon between two connector halves. The top half of the connector 30 does not need the coax cable 44 attached thereto as the coax cable may be clasped between the halves. The top half needs the shielding conductive polymer (32) to maximize the effectiveness of the shield.

In another embodiment, the structure for connector 30 could be manufactured, for example, through a molding procedure. The molding procedure may successively build up the connector 30 by forming the inner conductive polymer (34), the inner insulator (40), the outer conductive polymer (32), and the outer insulator 42 molded onto the coaxial cable 44.

Figures 7, 8, 9:
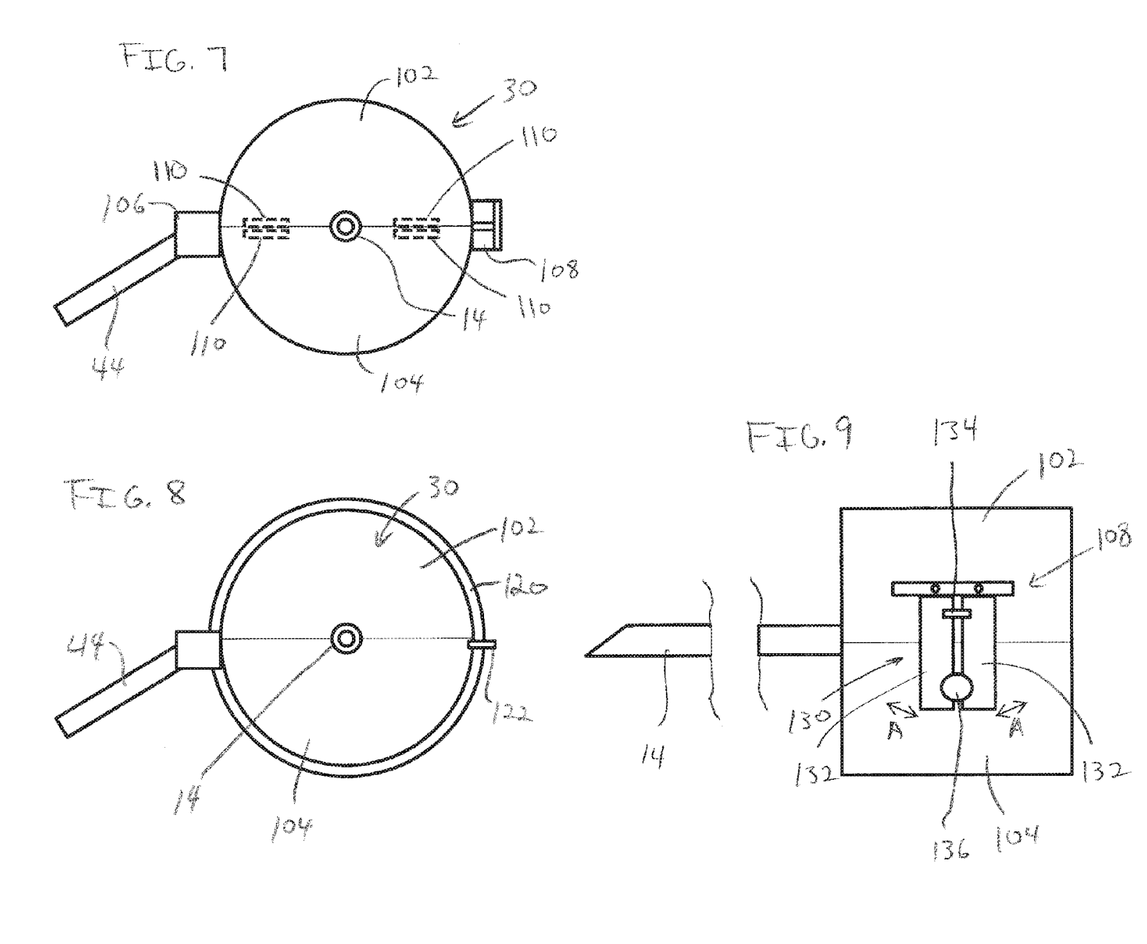
FIG. 7 is a front view showing a clamshell connector placed on a needle including a hinge and clasp for securing clamshell portions in accordance with the present principles.
FIG. 8 is a front view showing a clamshell connector placed on a needle including an elastic or mechanical clamp for securing clamshell portions in accordance with the present principles.
FIG. 9 is a side view showing a clamshell connector placed on a needle including an illustrative mechanical latch or clasp for securing clamshell portions in accordance with the present principles.

Referring to FIG. 7, a front view shows a connector 30 with clamshell portions 102 and 104 closed and a needle 12 coming out of the page. The split between the clamshell portions 102, 104 of the connector 30 may be made to include portions other than halves (e.g., one sector being 270 degrees and the other 90 degrees, etc.). Any number of methods can be employed to secure and or compress the two clamshells 102, 104 together onto the needle 14. In one embodiment, magnets 110 may be set within the clamshells 102, 104 such that they attract each other when placed around the needle 12. In another embodiment, a hinge 106 and a clasp, closure or securing mechanism 108 may be employed such that the two clamshells 102, 104 rotate relative to each other at the hinge 106 and snap fit together at the closure mechanism 108. In one embodiment, the closure mechanism 108 may work with magnets 110 or the magnets can replace the closure mechanism 108 for securing the clamshells 102, 104.

Referring to FIG. 8, another front view shows the connector 30 with the clamshell portions 102 and 104 closed and the needle 12 coming out of the page. The split between the clamshell portions of the connector 30 may be made to include portions other than halves (e.g., one sector being 270 degrees and the other 90 degrees, etc.). Other devices to secure the two clamshells 102, 104 together onto the needle 14 are illustratively depicted. A securing member 120 can fit over or around one or bother sides of the connector 30 to secure the two clamshells 102, 104 together. The member 120 may include a stretchable elastic sleeve, an elastic band, an elastic string, etc. In one embodiment, a stretchable band or string may wrap around the connector 30 and clings to itself (like a cling wrap or self-adhering elastic bandage, etc.) or to the outer surface of the connector 30. In another embodiment, a catch 122 (e.g., a pin, spike, hook etc.) may be employed to retain the member 120. In one embodiment, the member 120 may be stretchable and include a hook and loop portion to secure it on the connector 30. Member 120 may include a rigid clamp or other mechanism to secure the portions of the connector 30.

Referring to FIG. 9, in other embodiments, a clasp 108 may include a self-locking scissor type structure 130 including movable members 132 biased together by a biasing member 134. As a catch 136 from one clamshell portion 104 moves between the members 132, the members move apart in the directions of arrows "A" and recover to secure the clamshells 102, 104 portions together. Other mechanisms are also contemplated.

Referring again to FIG. 5, at the hub end, a bare needle surface 12, the signal trace ring electrode 24, and the outer shield 22 form three circular contact pads that the connector 30 can clamp onto. This design minimizes connector cost on the disposable needle and puts the more costly part of the connection on a reusable clamp that would connect to the needle and the other contacts. These embodiments can be implemented using additive manufacturing technologies such as, for example, conformal micro dispensing systems or inkjet deposition techniques.

An equivalent circuit formed using the connector 30 may include a sensor capacitance and interconnect capacitance (connections to the needle) forming a voltage divider circuit. Parasitic cable capacitance has significant impact on performance. A sufficiently high input resistance of an amplifier coupled to the coax cable 44 is also important as a resistive load on the sensor 10 and will create a high pass filter. In this example, a 30 kOhm amplifier resistance would lead to a −3 dB cutoff frequency of about 2.5 MHz.

There are some electronic strategies to lessen the effect of parasitic capacitance on performance. One such technique is called "driven shield". A key element in this method is to reduce parasitic current flow from the wire carrying the signal of interest by minimizing the electric field surrounding it. This employs a total of three conductors in the interconnect, a ground connection, a signal wire, and a shield surrounding the signal wire. The voltage on the signal wire is measured and the shield is driven with an exact replica of that voltage. Even though the signal wire has a parasitic capacitance to the shield there is no parasitic current flowing as there are no voltage changes over the parasitic capacitance. The ground wire is held at a steady voltage by the amplifier power supply and not driven by the sensor, thus its parasitic capacitance to other structures has no detrimental influence. Another technique includes using a capacitance canceling amplifier (CCA). To reduce external noise injection, a balanced amplifier may be used. This involves a sensor that has 2 signal traces that are both insulated from the outer shield and from the needle, and are surrounded by a shielding structure.

The present principles have been described in terms of a needle, and more particularly to a biopsy needle. However, the present principles may be applied to any instrument where a piezoelectric sensor (receiver), transmitter or transducer is needed. Such devices may include catheters, guidewires, endoscopes, implantable devices, etc. The present principles can provide a relatively low cost reusable connector device to connect with a built-in sensor conformally applied to an exterior surface. To keep the product cost down, the materials used need to be low cost, and the manufacturing process should be highly automated with large volume to avoid labor and equipment cost. The devices in accordance with the present principles provide a low form factor that is conformally formed and placed on a medical device or instrument. In particularly useful embodiments, the present principles are employed for ultrasound guided needle interventions, e.g., RF ablation, liver biopsy, nerve blocks, vascular access, abscess drainage, etc.

In interpreting the appended claims, it should be understood that:
   a) the word "comprising" does not exclude the presence of other elements or acts than those listed in a given claim;
   b) the word "a" or "an" preceding an element does not exclude the presence of a plurality of such elements;
   c) any reference signs in the claims do not limit their scope;
   d) several "means" may be represented by the same item or hardware or software implemented structure or function; and
   e) no specific sequence of acts is intended to be required unless specifically indicated.

Having described preferred embodiments for a connector for needles with piezoelectric polymer sensors (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A connector for making electrical contact with a plurality of ring-shaped contact pads of a medical needle, the ring-shaped contact pads being separated axially along a shaft of the medical needle and including an inner ring-shaped contact pad and two outer ring-shaped contact pads, the connector comprising:

an inner conductive body defining a first annular electrode for connecting to the inner ring-shaped contact pad on the medical needle;

an insulator formed on the inner conductive body; and an outer conductive body comprising a cavity having a cavity axis, the cavity being configured to receive therein a portion of the medical needle that includes the plurality of ring-shaped contact pads, wherein the cavity extends along the cavity axis through the first annular electrode for making electrical contact within the cavity with the first annular electrode and the inner ring-shaped sensor contact pad on the medical needle;

wherein the outer conductive body is formed over the insulator and surrounds the inner conductive body and is electrically isolated from the inner conductive body by the insulator;

wherein the outer conductive body defines a second annular electrode and a third annular electrode, the second annular electrode and the third annular electrode being electrically connected together by the outer conductive body and being disposed along the cavity axis and axially on opposite sides of the first annular electrode for making electrical contact with the two outer ring-shaped contact pads.

2. The connector as recited in claim 1, further comprising the medical needle and wherein the medical needle further includes:

a conductive surface having a piezoelectric polymer sensor formed as a layer thereon, the piezoelectric polymer sensor at a distal portion of the needle and in contact with the conductive surface such that the conductive surface provides a first electrical contact with an innermost surface of the piezoelectric polymer sensor, the piezoelectric polymer sensor further including a second electrical contact disposed on an outermost surface of the piezoelectric polymer sensor;

a first insulator layer;

a signal trace being in electrical contact with the second electrical contact;

a second insulator layer; and a conductive shield, wherein the first insulator layer, the second insulator layer and the conductive shield are formed as coaxial layers on the conductive surface of the medical needle such that the first insulator layer is innermost with respect to the medical needle, and such that the conductive shield is outermost with respect to the medical needle, and such that the signal trace and the second insulator layer are sandwiched be the first insulator layer and the conductive shield, and such that the signal trace is disposed between the first insulator layer and the second insulator layer, the coaxial layers extending from the distal portion of the medical needle to a proximal portion of the medical needle;

wherein the signal trace extends along the medical needle from the distal portion of the medical needle to the proximal portion of the medical needle and is in electrical contact with the inner ring-shaped contact pad of the medical needle at the proximal portion of the medical needle:

wherein the two outer ring-shaped contact pads of the medical needle contact a portion of the conductive surface of the medical needle and a portion of the conductive shield and wherein the medical needle and the connector are arranged such that:

the inner ring-shaped contact pad of the medical needle is in electrical contact with the first annular electrode, and such that:

the portion of the conductive surface of the medical needle and the portion the conductive shield are in electrical contact with the second annular electrode and the third annular electrode defined by the outer conductive body of the connector.

3. The connector as recited in claim 1, wherein the inner conductive body and the outer conductive body include conductive polymers, and the inner conductive body, the outer conductive body and the insulator are molded.

4. The connector as recited in claim 1, further comprising an insulating coating formed on an outer surface of the outer conductive body.

5. The connector as recited in claim 1, wherein the connector is configured in clamshell portions that are configured to close to form the connector on the medical needle.

6. The connector as recited in claim 5, further comprising a hinge for closing the clamshell portions.

7. The connector as recited in claim 5, further comprising a securing feature to maintain the clamshell portions on the medical needle.

8. The connector as recited in claim 7, wherein the securing feature includes an elastic feature that stretches over an outer surface of the connector.

9. The connector as recited in claim 1, further comprising a coaxial cable having a center conductor and a shield, wherein the center conductor and the shield each connect to one of the inner conductive body and the outer conductive body.

10. A connector for making electrical contact with a plurality of ring-shaped contact pads of a medical needle, the ring-shaped contact pads being separated axially along a shaft of the medical needle and including an inner ring-shaped contact pad and two outer ring-shaped contact pads, the connector, comprising:

a first conductive body configured to receive therein the medical needle, the first conductive body contacting an outer surface of the medical needle at a first electrical contact and at a second electrical contact, the first conductive body forming a cavity having a cavity axis;

a second conductive body defining a first annular electrode disposed within the cavity and contacting the outer surface of the medical needle at a third electrical contact, the third electrical contact being disposed between the first and the second electrical contact, wherein the cavity is configured to receive therein a portion of the medical needle that includes the plurality of ring-shaped contact pads, wherein the cavity extends along the cavity axis through the first annular electrode for making electrical contact within the cavity with the first annular electrode and the inner ring-shaped sensor contact pad on the medical needle;

an insulating material disposed between the first and second conductive body in the cavity to electrically isolate the first and second conductive bodies from each other; and a coaxial cable having a center conductor and a shield, wherein the central conductor and the shield each connect to one of the first and second conductive bodies, wherein the first conductive body defines a second annular electrode and a third annular electrode, the second annular electrode and the third annular electrode being electrically connected together by the first conductive body and being disposed along the cavity axis and axially on opposite sides of the first annular electrode for making electrical contact with the two outer ring-shaped contact pads.

11. The connector as recited in claim 10, wherein the medical needle comprises one or more piezoelectric polymer sensors formed thereon and the first electrical contact includes the needle, the second electrical contact includes a shield for an electrical trace for the sensor and the third electrical contact includes a connection to a sensor electrode.

12. The connector as recited in claim 10, wherein the first conductive body and the second conductive body include conductive polymers, and the first conductive body, the second conductive body and insulating material are molded on the medical device.

13. The connector as recited in claim 10, further comprising an insulating coating formed on an outer surface of the first conductive body.

14. The connector as recited in claim 10, wherein the connector is configured as clamshell portions that close to form the connector on the medical device.

15. A connector, comprising:
- a needle including a plurality of ring-shaped contact pads separated axially along a shaft of the medical needle and including an inner ring-shaped contact pad and two outer ring-shaped contact pads;
- an inner conductive body defining a first annular electrode configured to connect to the inner ring-shaped contact pad on the medical needle;
- an insulator formed on the inner conductive body;
- an outer conductive body comprising a cavity having a cavity axis, the cavity being configured to receive therein a portion of the medical needle that includes the plurality of ring-shaped contact pads, wherein the cavity extends along the cavity axis through the first annular electrode for making electrical contact within the cavity with the first annular electrode and the inner ring-shaped sensor contact pad on the medical needle;
- wherein the outer conductive body is formed over the insulator and surrounds the inner conductive body and is electrically isolated from the inner conductive body by the insulator, wherein the outer conductive body defines a second annular electrode and a third annular electrode, the second annular electrode and the third annular electrode being electrically connected together by the outer conductive body and being disposed along the cavity axis and axially on opposite sides of the first annular electrode for making electrical contact with the two outer ring-shaped contact pads;
- an insulating coating formed on an outer surface of the outer conductive body; and
- a coaxial cable having a center conductor and a coaxial shield, wherein the central conductor connects to the inner conductive body and the coaxial shield connects to the outer conductive body.

* * * * *